(12) United States Patent
Eberheim et al.

(10) Patent No.: US 8,581,575 B2
(45) Date of Patent: Nov. 12, 2013

(54) CONDUCTIVITY SENSOR WITH SWITCHING BETWEEN TRANSMITTING AND RECEIVING COIL

(75) Inventors: Andreas Eberheim, Waldheim (DE); Thomas Nagel, Wilsdruff (DE); Andre Thieme, Greithain (DE); Hendrik Zeun, Chemnitz (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 711 days.

(21) Appl. No.: 12/801,557

(22) Filed: Jun. 15, 2010

(65) Prior Publication Data
US 2011/0001490 A1    Jan. 6, 2011

(30) Foreign Application Priority Data
Jun. 17, 2009   (DE) .......................... 10 2009 026 998

(51) Int. Cl.
*G01R 33/12*  (2006.01)
(52) U.S. Cl.
USPC ............ 324/204; 324/445; 324/439; 324/693
(58) Field of Classification Search
USPC ................................. 324/445, 204, 439, 693
See application file for complete search history.

(56) References Cited

U.S. PATENT DOCUMENTS

| | | | | |
|---|---|---|---|---|
| 3,806,798 A * | 4/1974 | Gross | ............................. | 324/445 |
| 5,157,332 A * | 10/1992 | Reese | ............................. | 324/445 |
| 5,341,102 A * | 8/1994 | Akiyama et al. | ............... | 324/445 |
| 5,793,214 A * | 8/1998 | Wakamatsu | ................... | 324/601 |
| 6,812,709 B2 * | 11/2004 | Wieland et al. | ................ | 324/445 |

FOREIGN PATENT DOCUMENTS

| | | |
|---|---|---|
| DE | 41 16 468 C2 | 11/1992 |
| DE | 197 47 273 A1 | 4/1999 |
| DE | 203 17 771 U1 | 7/2004 |
| EP | 1 384 997 B1 | 1/2004 |

* cited by examiner

Primary Examiner — Richard Isla Rodas
(74) Attorney, Agent, or Firm — Bacon & Thomas, PLLC

(57) ABSTRACT

An inductively working sensor for determining the conductivity of a liquid medium. The sensor includes: at least one transmitting circuit, which is designed to deliver an input signal for a transmitting coil, in order to produce in the transmitting coil an alternating electromagnetic field, which causes a ring-shaped electrical current in the liquid medium; at least one receiving circuit, which is designed to evaluate a received signal produced by the ring-shaped electrical current in a receiving coil; a first coil; a second coil, which is arranged at a distance from the first coil; a switching means for switching between a first switch state and a second switch state, wherein, in the first switch state, the first coil, serving as transmitting coil, is coupled with one of the transmitting circuits; and the second coil, serving as receiving coil, is coupled with one of the receiving circuits, and wherein, in the second switch state, the second coil, serving as transmitting coil, is coupled with one of the transmitting circuits, and the first coil, serving as receiving coil, is coupled with one of the receiving circuits.

21 Claims, 4 Drawing Sheets

200
CONDUCTIVITY SENSOR WITH SWITCHING BETWEEN TRANSMITTING AND RECEIVING COIL

TECHNICAL FIELD

The invention relates to an inductively working sensor, as well as to a method for determining conductivity of a liquid medium.

BACKGROUND DISCUSSION

In process automation technology, field devices are often employed, which serve to register and/or influence process variables. Examples of such field devices are fill level measuring devices, mass flow measuring devices, pressure and temperature measuring devices etc., which, as sensors, register the corresponding process variables, fill level, flow, pressure, and temperature, respectively.

In principle, all devices which are used near to the process and which deliver or work with process-relevant information are referred to as field devices.

A plurality of such field devices is produced and sold by the firm, Endress+Hauser.

Applied for determining the conductivity of a liquid medium are inductively working sensors, which have a transmitting coil, as well as a receiving coil. The receiving coil is arranged at a distance from the transmitting coil. Produced by the transmitting coil is an alternating electromagnetic field, which acts on the charged species (e.g. ions) in the liquid medium, and brings about a corresponding electrical current flow in the medium. Through this electrical current flow, an electromagnetic field arises at the receiving coil, which induces a received signal in the receiving coil. This received signal can be evaluated and taken into consideration for determining the conductivity of the liquid medium.

When inductively measuring conductivity, a risk exists that, as a result of coil defects (such as, for example, winding shorts, leakage currents or damage to the coil, etc.), defective measured values will be ascertained, and that the defectiveness of these measured values will not be recognized.

SUMMARY OF THE INVENTION

An object of the invention is to improve the reliability and accuracy of conductivity values delivered by an inductively working sensor.

The inductively working sensor of the invention for determining conductivity of a liquid medium includes: at least one transmitting circuit, which is designed to deliver an input signal for a transmitting coil, in order to produce in the transmitting coil an alternating electromagnetic field, which causes a ring-shaped electrical current in the liquid medium; at least one receiving circuit, which is designed to evaluate a received signal produced by the ring-shaped electrical current in a receiving coil; a first coil; and a second coil arranged at a distance from the first coil. The inductively working sensor moreover includes a switching means for switching between a first switch state and a second switch state, wherein, in the first switch state, the first coil, serving as a transmitting coil, is coupled with a transmitting circuit, and the second coil, serving as a receiving coil, is coupled with a receiving circuit; and wherein, in the second switch state, the second coil, serving as a transmitting coil, is coupled with one of the transmitting circuits, and the first coil, serving as a receiving coil, is coupled with one of the receiving circuits.

Through the switching means of the invention, it is enabled that the first and the second coils are alternately used as the transmitting coil. When a coil is operated as the transmitting coil, an input signal is applied to the coil, and an electrical current flow arises in the coil. Therefore, in the case of a coil being employed as the transmitting coil, it can easily be checked whether the coil is functioning correctly, by, for example, checking the relationship between the input signal and coil current. In the case of a coil being operated as the receiving coil, in contrast, it is not provided that a function checking of the coil can be conducted from the receiving circuit. There exists, consequently, the risk that a damaged receiving coil remains, at least for a certain time, undiscovered, and that it delivers defective measured values. It would, consequently, be important, to also be able to check the functioning of the receiving coil in a simple manner.

In the case of the solution of the invention, both the first coil and the second coil can alternately be coupled with one of the transmitting circuits. In this way, a continuous monitoring of both coils can be implemented with little effort. Through this, it is assured that the functioning of a coil which is operated as the receiving coil can also regularly be checked, in order to detect errors in a timely manner. In this way, the reliability of the ascertained measured values is noticeably improved.

According to a preferred form of embodiment, the inductance of the particular coil coupled with a transmitting circuit can be ascertained from the transmitting circuit. In this way, the inductances of the first coil and the second coil can be regularly ascertained. When the coil inductances are known as precisely as possible, the conductivity of the medium can be ascertained with a better accuracy than before. In such case, it is especially to one's advantage to also be able exactly to follow temperature-related fluctuations of the inductances, especially of the inductance of the receiving coil. This is enabled by the switching function of the invention.

Preferably, the coils are embodied as toroidal coils. Here and in the following, the term "toroidal coil" refers to a coil with a closed magnetic path. The coil can have a magnetic or magnetizable core, or it can be embodied as a coreless coil. The magnetic path must be closed, or at least be bridged by an air gap. The shape of the toroid is not, in such case, of importance. A circular ring is the simplest shape; any other desired shapes (such as, for example, ellipses, rectangles or other polygons) are, however, equally thinkable. Such a toroidal coil has a central axis, which, in the case of a cylindrically symmetrical circular toroidal coil, is a rotational symmetry axis. In the event that the toroidal coil does not exhibit cylindrical symmetry, but is instead, for example, embodied as an ellipse or as a polygon, the central axis extends, for example, through the midpoint of the polygon, or through a central point within the ellipse located between the elliptical focal points.

The transmitting and receiving coils can, for example, be arranged coaxially, one after the other; coplanarly and axially parallel (i.e. next to one another in a plane) or coaxially coplanarly (i.e. nested in one another). In the latter case, the coils have different diameters, wherein the inner diameter of the first coil is, as a rule, greater than the outer diameter of the second coil. The transmitting and receiving coils can also be arranged inclined toward one another. In this case, it is especially preferred that the central axes of the two coils intersect, e.g. come together to form an angle of 90°.

BRIEF DESCRIPTION OF THE DRAWINGS

The invention will now be explained in greater detail on the basis of several examples of embodiments presented in the drawing, the figures of which show as follows.

DETAILED DISCUSSION IN CONJUNCTION WITH THE DRAWINGS

Figure 1:
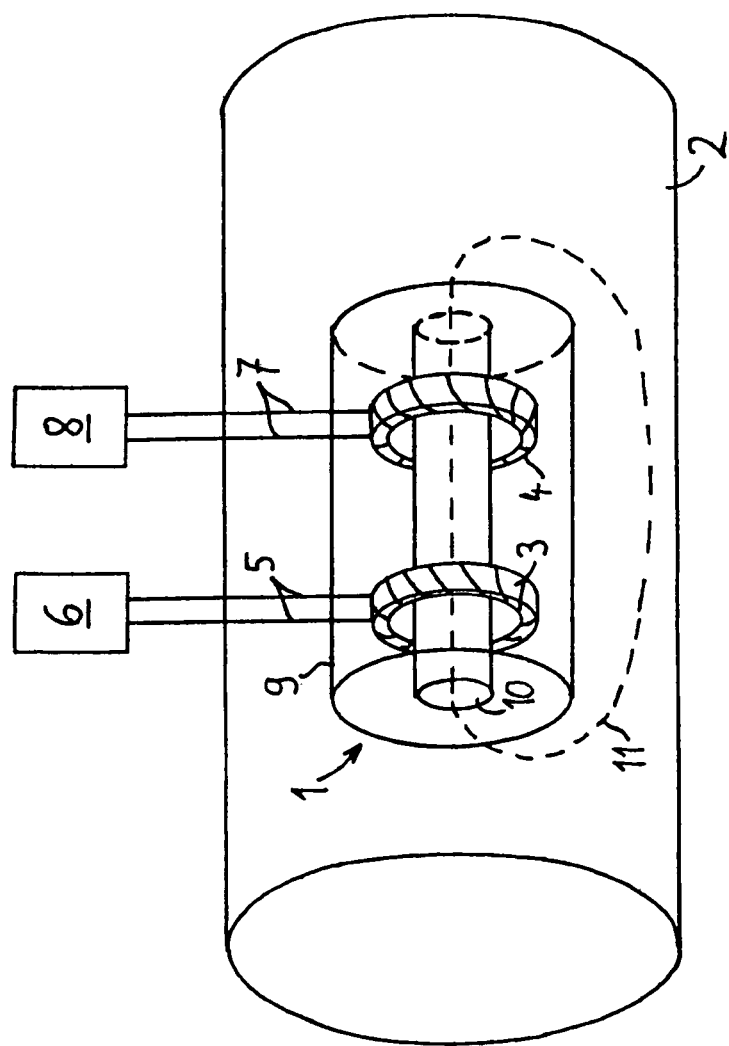
FIG. 1 is a construction of an inductively working sensor for determining conductivity.

FIG. 1 shows the construction of an inductively working sensor for determining the conductivity of a liquid medium. In the illustrated example, the sensor 1 is placed inside a pipe 2, through which a liquid medium is flowing. In the case of use in food, pharmaceutical or chemical production plants, the pipe 2 can have, for example, a standardized diameter of 40 mm, 50 mm or 80 mm. The inductively working sensor 1 includes a transmitting coil 3, which is embodied as a toroidal coil, as well as a receiving coil 4, which is arranged on the same axis as the transmitting coil 3, and which is likewise embodied as a toroidal coil. Via supply lines 5, the transmitting coil 3 is connected with a transmitting circuit 6, which produces an input signal for the transmitting coil 3. Via supply lines 7, the receiving coil 4 is connected with a receiving circuit 8, which evaluates the received signal received by the receiving coil 4. The transmitting coil 3 and the receiving coil 4 are arranged within a sensor housing 9, which has an opening 10. Liquid medium can flow through the opening 10.

For performing the conductivity measuring, the transmitting circuit 6 produces for the transmitting coil 3 an input signal, which, for example, can have a frequency of about 1 kHz. The transmitting coil 3 then produces an alternating electromagnetic field, which acts upon the movable ions of the liquid medium, which is located within the opening 10. The flow of ions brought about within the opening 10 leads to a corresponding return flow outside of the sensor housing 9, so that an overall ring-shaped electrical current 11 results, which runs through the opening 10. The electrical current level of the ring-shaped electrical current 11 depends, in such case, on the concentration, mobility and valence of the ions contained in the liquid medium, and, thus, on the electrical conductivity of the liquid medium. Through the ring-shaped electrical current 11, an alternating electromagnetic field is brought about within the receiving coil 4. This alternating electromagnetic field induces in the receiving coil 4 a received signal, which is evaluated by the receiving circuit 8. On the basis of this received signal, the receiving circuit 8 can determine the conductivity of the liquid medium located within the pipe 2.

The conductivity sensor 1 can additionally have a temperature sensor (not shown), which provides temperature signals dependent on the temperature of the medium.

Figure 2:
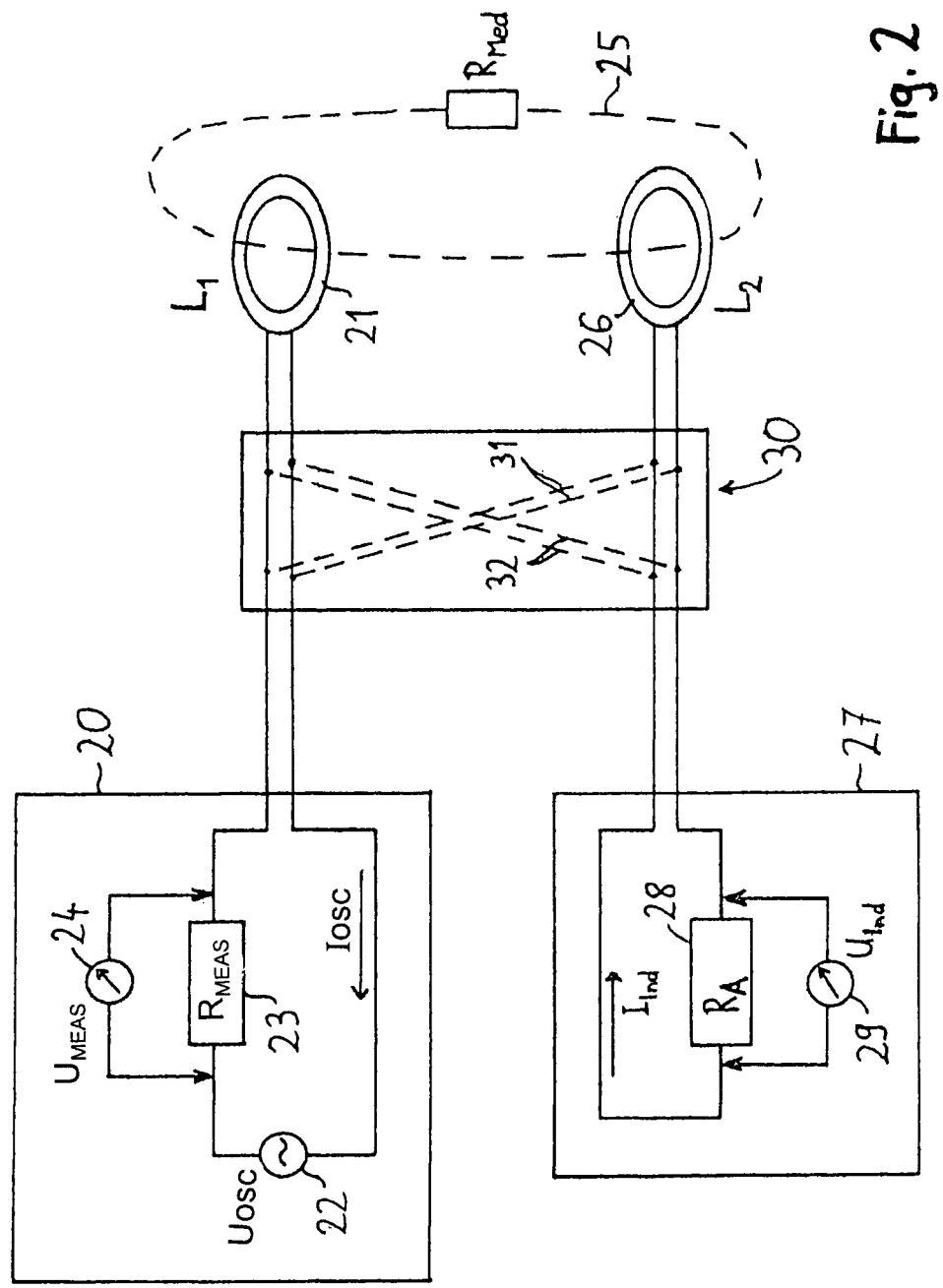
FIG. 2 is a circuit of a sensor for determining conductivity according to the present invention.

FIG. 2 shows a circuit diagram for the conductivity sensor illustrated in FIG. 1. The transmitting circuit 20 is designed to produce an input signal for the first coil 21. The first coil 21 is preferably embodied as a toroidal coil and has $N_1$ windings. The inductance of the first coil 21 is referred to in the following with $L_1$.

For producing the input signal, the transmitting circuit 20 includes an alternating voltage source 22, which produces an alternating voltage $U_{Osc}$ with a frequency of about 1 kHz. This alternating voltage $U_{Osc}$ is fed to the first coil 21 via the measuring resistor 23, which has the value $R_{MEAS}$. In this way, an alternating current $I_{Osc}$ is formed in the transmitting circuit. This alternating electrical current $I_{Osc}$ can be captured by sensing and evaluating by means of a measuring arrangement 24 the voltage $U_{MEAS}$ dropping across the measuring resistor 23. Consequently, both the alternating voltage $U_{Osc}$, as well as the alternating electrical current $I_{Osc}$ brought about thereby, can be monitored within the transmitting circuit 20.

Via the first coil 21, there is produced in the liquid medium a ring-shaped electrical current 25, whose strength depends on the conductivity or on the specific resistance $R_{Med}$ of the liquid medium. Through the ring-shaped electrical current 25, a received signal is induced in the second coil 26. The second coil 26 is likewise embodied as a toroidal coil, and has $N_2$ windings. The inductance of the second coil 26 is referred to in the following with $L_2$. The received signal induced in the second coil 26 is fed to the receiving circuit 27 and is evaluated there. In an advantageous form of embodiment, an additional resistor 28 with the value $R_A$, which serves to limit the electrical current $I_{Ind}$ in the receiving circuit, is provided in the receiving circuit. Especially when the conductivity sensor is used in an explosion hazard environment, a limiting of the electrical current is necessary for safety reasons. The level of the electrical current $I_{Ind}$ in the receiving circuit can be ascertained by means of a measuring arrangement 29, which captures and evaluates the voltage $U_{Ind}$ falling across the resistor 28. The thusly ascertained voltage $U_{Ind}$ represents the strength of the received signal and can, consequently, be taken into consideration in determining the conductivity of the liquid medium.

The circuit arrangement shown in FIG. 2 can register for the first coil 21 both the applied alternating voltage $U_{Osc}$ as well as the electrical current $I_{Osc}$ caused thereby. In this way, the transmitting circuit 20 is able to monitor the functioning of the first coil 21. Moreover, based on the alternating voltage $U_{Osc}$ and the alternating electrical current $I_{Osc}$, the complex impedance Z in the transmitting circuit can also be ascertained, from whose imaginary part the inductance $L_1$ of the first coil 21 can be derived.

In order to enable a monitoring of the second coil 26, a switching unit 30, which can be switched into two different switch states, is provided in the sensor of the invention. In the first switch state of the switching unit 30, the first coil 21 is connected with the transmitting circuit 20, while the second coil 26 is connected with the receiving circuit 27. When the switching unit 30 is switched to the second switch state, the two coils 21 and 26 are then transposed with one another. In the second switch state, the second coil 26 is connected with the transmitting circuit 20 via the connecting lines 31 and is operated as the transmitting coil, whereas the first coil 21 is connected with the receiving circuit 27 via the connecting lines 32, and is operated as the receiving coil.

In the case of the solution of the invention, each the coils 21, 26 can be selectively connected either with the transmitting circuit 20 or with the receiving circuit 27. When a particular coil is connected with the transmitting circuit 20, then both the alternating voltage $U_{Osc}$ applied to the coil as well as the electrical current $I_{Osc}$ flowing through the coil can be registered by the transmitting circuit 20. In this way, the proper functioning of each of the two coils 21 and 26 can be checked.

Optionally, the inductance of the coil coupled with the transmitting unit 20 can be ascertained based on the alternating voltage $U_{Osc}$ and the electrical current $I_{Osc}$. In this connection, the complex valued impedance $Z=U_{Osc}/I_{Osc}$ is ascertained.

Figure 3:
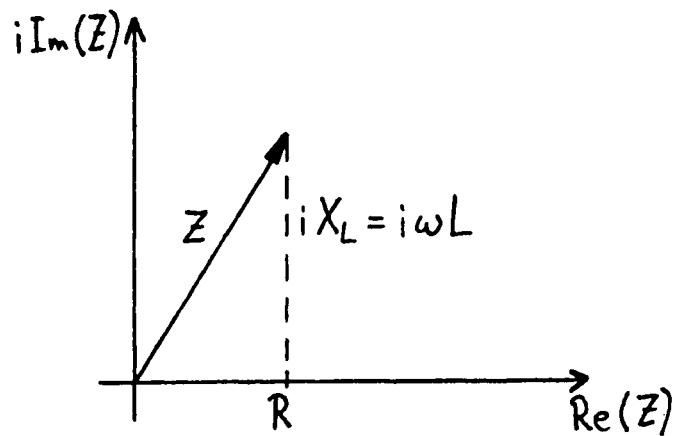
FIG. 3 is a graph of impedance of the transmitting circuit in the complex plane.

FIG. 3 shows the thusly ascertained impedance Z in the complex plane. The real part R of the impedance Z refers to the ohmic part of the impedance, while the imaginary part $i \cdot X_L$ refers to the inductive reactance of the coil coupled with the transmitting circuit. The inductive reactance $X_L$ can be written as $X_L = i \cdot \omega \cdot L$, wherein $\omega$ refers to the angular frequency of the alternating voltage, and L refers to the coil inductance. As a result, the inductance L of the coil which is coupled which with the transmitting circuit 20 can be ascertained from the imaginary part $i \cdot X_L$ of the impedance Z and the angular frequency $\omega$. From the inductance L, the coil quality $Q = \omega L/R$ can also then be ascertained.

Since either the first coil 21 or the second coil 26 can, with the assistance of the switching unit 30, selectively be interconnected with the transmitting circuit 20, both the inductance $L_1$ of the first coil 21 as well as the inductance $L_2$ of the second coil 26 can be ascertained by the transmitting circuit 20. The inductance $L_2$ of the second coil 26, however, is especially of great interest for determining the conductivity, since a knowledge of $L_2$ enables a more exact determining of the conductivity of the liquid medium, as the following explanation shows:

The conductivity or the specific resistance $R_{Med}$ of the liquid medium can, for example, be calculated according to the following formula:

$$U_{Ind} = \frac{N_2}{N_1} \cdot \frac{1}{1 + N_2^2 \cdot R_{Med} \cdot \left( \frac{1}{R_A} + \frac{1}{i \cdot \omega \cdot L_2} \right)} \cdot U_{Osc}$$

In this formula, $N_1$ refers to the number of turns in the transmitting coil, $N_2$ to the number of turns in the receiving coil, $U_{Osc}$ to the alternating voltage in the transmitting circuit, $U_{Ind}$ to the induced alternating voltage in the receiving circuit, $\omega$ to the angular frequency of the alternating voltage in the transmitting circuit and $R_A$ to the ohmic resistance inserted into the receiving circuit for reasons of Ex-protection. When the formula provided above is solved for the resistance in the liquid medium $R_{Med}$, there results:

$$R_{Med} = \frac{\left( \frac{N_2}{N_1} \cdot \frac{U_{Osc}}{U_{Ind}} - 1 \right)}{N_2^2 \cdot \left( \frac{1}{R_A} + \frac{1}{i \cdot \omega \cdot L_2} \right)}$$

In the case in which $R_A \ll \omega \cdot L_2$, the term containing $L_2$ is negligible. This procedure leads, however, to inexact results, especially when the relationship $R_A \ll \omega \cdot L_2$ is no longer true, thus when the ohmic resistance $R_A$ in the receiving circuit is no longer negligible with respect to the term $\omega \cdot L_2$. In this case, the measured value is dependent on the inductance $L_2$ of the secondary coil. Taking into consideration the inductance $L_2$ leads, then, to a significant improvement in the accuracy of the conductivity measured values obtained.

The inductance $L_2$ of the second coil 26 is, in general, dependent on temperature. The inductance depends on core permeability, and the core permeability is a function of temperature. Therefore, the inductance $L_2$ of the second coil 26 changes as a function of the temperature, wherein, depending on the core material, the change moves in the order of magnitude of 10% per 100° C. In order to be able to compensate for this temperature dependence of the inductance $L_2$, it is important in each case to be able to determine anew the inductance $L_2$ as a function of the ambient temperature. This is enabled by the switching unit 30 of the invention.

Alternatively or in addition to determining the inductance $L_2$, the switching unit 30 of the invention can be utilized for monitoring the coil parameters, and thus for monitoring the functionality of the second coil 26.

A number of coil defects can be detected immediately by monitoring the relationship between the alternating voltage $U_{Osc}$ and the alternating electrical current $I_{Osc}$, so that an error of such a sort can be recognized as soon as possible.

One possible defect is a line interruption, either in the region of the supply cable (for instance, through a breaking of the supply cable), or in the region of the coil itself, where, for example, a breaking of the coil wire could occur. When the affected coil is coupled with the transmitting circuit 20, it is detected, that, in spite of the applied alternating voltage $U_{Osc}$, no electrical current flow $I_{Osc}$ can occur. In this case, a corresponding defect report would be produced.

A further possible defect is the occurrence of a so-called winding short. In the case of a winding short, an undesired electrical contact between neighboring toroidal coil windings arises, the cause of which, for example, can lie in a damaged insulation of the coil wire. The coil wire is typically insulated by a thin lacquer layer with, for example, a thickness of 30 μm, and this lacquer insulation can have damaged spots. As a result of these damaged spots, a short circuit between neighboring toroidal coils or the occurrence of leakage currents can then come about. As a result of this, a counterinductance, for example, can build up, and the inductance of the coil strongly decreases. By monitoring by means of the transmitting circuit 20 the relationship between the alternating voltage $U_{Osc}$ and the electrical current $I_{Osc}$ flowing through the coil, this sinking of the inductance L as a result of a winding short can immediately be recognized. As a result of the sinking inductance, a winding short also leads to a corresponding sinking of the coil quality $Q = \omega L/R$.

A further possible defect is that a short circuit occurs on the circuit board, on the coil support or in the supply lines to the coil. Alternatively, leakage currents could occur. In these situations, in the case of an applied alternating voltage $U_{Osc}$, the electrical current through the coil $I_{Osc}$ increases, and this rise can be detected by the transmitting circuit 20.

A further possible defect is that the coil core of the coil coupled with the transmitting circuit 20 is damaged. Damage to the relatively brittle coil core can occur, for example, as a result of impacts or vibrations. This can especially lead to a crack in the coil core. Since a coil core generally amplifies the inductance of a coil, such damage leads, as a rule, to a corresponding lessening of the inductance L of the coil. Since the relationship between $U_{Osc}$ and $I_{Osc}$—and also especially the phase shift between the two oscillating variables—is monitored by the transmitting circuit 20, such a change of the inductance L of the coil (as, for example, arises through damage to the coil core), can immediately be recognized. Thus, by monitoring the inductance L or the coil quality Q, damage to the coil core can be recognized.

A further possible defect is a drifting of the inductance of the coil, which can occur as a result of aging phenomena. The slow changes to the coil parameters caused by this drift leads, as a result, to a change in the inductance L of the coil, and thereby also to a change in the coil quality Q. Such creeping changes in the inductance can also be recognized by monitoring the relationship between $U_{Osc}$ and $I_{Osc}$.

A further possible defect involves liquid entering into a coil monitored by the transmitting circuit 20. Through the liquid the entering into the coil, overcoupling to the liquid medium rises. In this way, the inductance L as well as the coil quality Q of the coil change, and this can be recognized by the transmitting circuit 20.

For monitoring the particular coil which is connected to the transmitting circuit 20 via the switching unit 30, range limits for one or more of the following variables can be established, for example, by the transmitting circuit 20: $U_{Osc}$, $I_{Osc}$, the phase angle between $U_{Osc}$ and $I_{Osc}$, the impedance Z, the inductance L, the coil quality Q, etc. In this way, allowed ranges for the coil parameters can be defined, in order to assure an orderly functioning of the two coils 21, 26 with the assistance of these allowed ranges. Through a comparison of the currently ascertained coil parameters with these predetermined range limits, especially a possible defect of the coil can immediately be recognized. In this case, the plant can, for example, then be turned off, and the conductivity sensor replaced. In the case of less serious errors, it is, in certain circumstances, also possible to correct the currently ascertained conductivity according to the ascertained coil defect.

There are various possibilities for implementing the switching unit 30 illustrated in FIG. 2. A first possibility is to implement the switching unit 30 shown in FIG. 2 as a mechanical switching unit with, for example, one or more relays. In this form of embodiment, the switching between the two coils 21 and 26 occurs by an actual switching of contacts.

Figure 4:
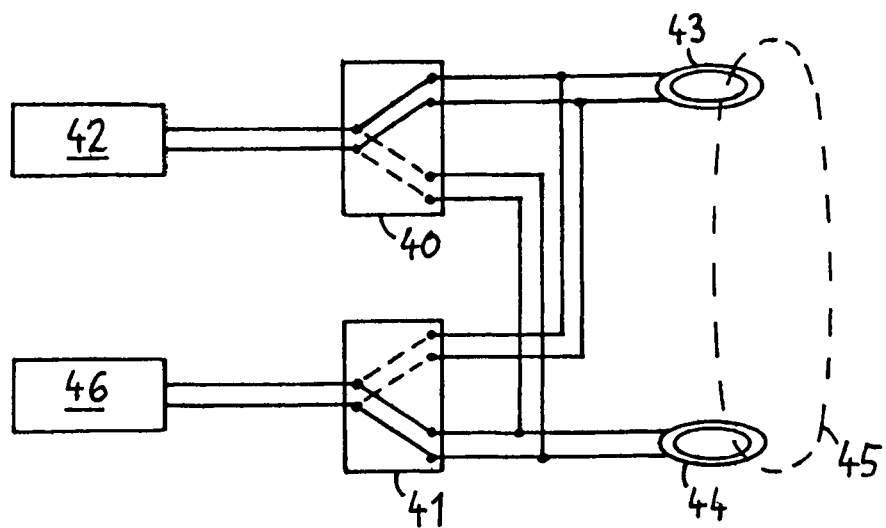
FIG. 4 is a first form of embodiment of the invention.

FIG. 4 shows another form of embodiment, in the case of which the switching functionality is implemented by means of a demultiplexer 40 and a multiplexer 41. With the assistance the demultiplexer 40, the input signals produced by the transmitting circuit 42 can selectively be conveyed either to the first coil 43 or to the second coil 44. When the demultiplexer 40 is in its first switch position, (which is illustrated in FIG. 4 with solid lines), then the input signals produced by the transmitting circuit 42 arrive at the first coil 43, which, in this case, is operated as the transmitting coil. The first coil 43 produces an alternating electromagnetic field, which is transmitted to the second coil 44 via a ring-shaped electrical current 45 in the medium. In the example illustrated in FIG. 4, the multiplexer 41 is in its first switch state, and the second coil 44 is connected with the receiving circuit 46. This first switch state of the multiplexer 41 is shown in FIG. 4 with solid lines. The received signals received by the second coil 44 are then fed to the receiving circuit 46 and evaluated there.

When, in contrast, both the demultiplexer 40 and the multiplexer 41 are switched to their respective second switch states, the transmitting circuit 42 is then connected via the demultiplexer 40 with the second coil 44, and the second coil 44 is operated as the transmitting coil. The first coil 43 is operated as the receiving coil and is, via the multiplexer 41, connected with the receiving circuit 46, which evaluates the signals received by the first coil 43. The demultiplexer 40 shown in FIG. 4 can, for example, be constructed from two 1:2-demultiplexers, while the multiplexer 41 can be constructed from two 2:1-multiplexers. Both the demultiplexer 40 as well as the multiplexer 41 can be switched with the assistance of electrical control signals, in order selectively to connect either the first coil 43 or the second coil 44 with the transmitting circuit 42. In this way, the coil parameters of the first coil 43 or the coil parameters of the second coil 44 can be checked selectively.

Figure 5:
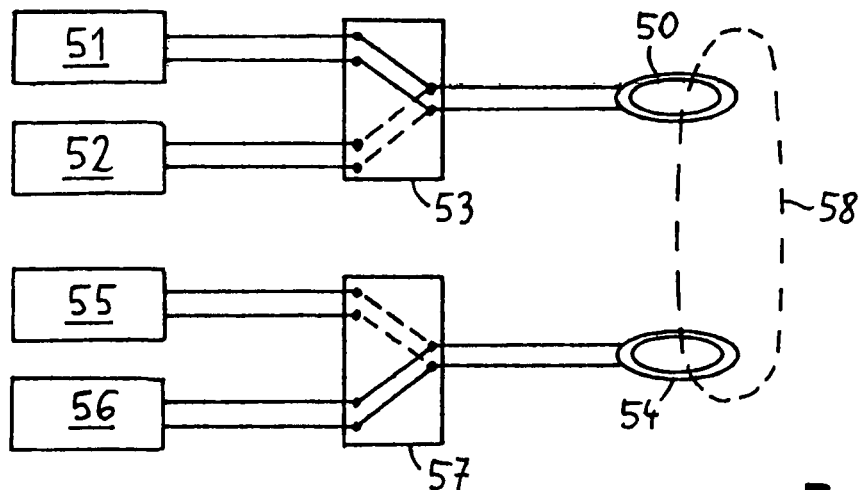
FIG. 5 is an alternative form of embodiment of the invention.

FIG. 5 shows an alternative form of embodiment of the invention, in the case of which, in contrast to FIG. 4, a separate transmitting circuit, as well as a separate receiving circuit, is provided for each coil. A transmitting circuit 51, as well as a receiving circuit 52, is associated with the first coil 50. Via the first switching unit 53, the first coil 50 can selectively be connected with either the transmitting circuit 51 or with the receiving circuit 52. A transmitting circuit 55, as well as a receiving circuit 56, is associated with the second coil 54. Via the second switching unit 57, the second coil 54 can selectively be connected with the transmitting circuit 55 or with the receiving circuit 56.

When both the first switching unit 53 and the second switching unit 57 are in a first switch state (which is illustrated with solid lines) the first coil 50 is then connected with the transmitting circuit 51, while the second coil 54 is connected with the receiving circuit 56. Therefore, the first coil 50 is operated as the transmitting coil, and it produces in the medium a ring-shaped electrical current 58, which is received by the second coil 54 and evaluated in the receiving unit 56.

When, in contrast, both the first switching unit 53 as well as the second switching unit 57 is, in each case, switched to its respective second switch state, the second coil 54 is then connected with the transmitting circuit 55, while the first coil 50 is connected with the receiving circuit 52. In this case, the second coil 54 is thus operated as the transmitting coil (which produces the ring-shaped electrical current 58 in the medium), wherein the received signals induced in the first coil 50 can then be evaluated by the receiving circuit 52. In the case of the forms of embodiment illustrated in FIG. 5, each of the two coils 50, 54 can be operated both as the transmitting coil, as well as the receiving coil. In each case, whenever a coil is connected with one of the transmitting circuits 51, 55, the respective transmitting circuit can also perform a function check or determine the inductance of the respective coil.

In the case of the form of embodiment illustrated in FIG. 5, the switching between transmitting and receiving modes occurs with the assistance of the switching units 53 and 57. In an alternative form of embodiment, the transmitting circuit and the receiving circuit are embodied as so-called tri-state circuits, wherein either the transmitting circuit or the receiving circuit is switched to a high-resistance state, in order to switch between the transmitting and receiving modes.

Figure 6:
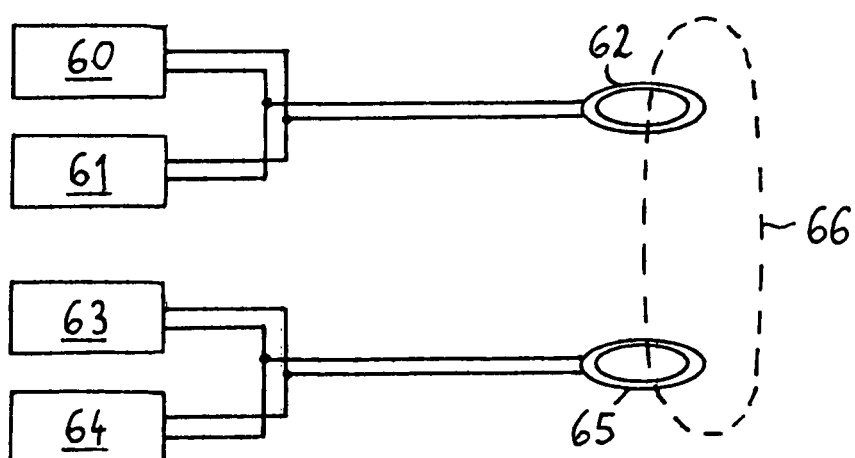
FIG. 6 is another form of embodiment of the invention.

Such a form of embodiment is shown in FIG. 6. A transmitting circuit 60 and a receiving circuit 61 are connected with a first coil 62, while a transmitting circuit 63 as well as a receiving circuit 64 are connected with a second coil 65. The transmitting circuits 60, 63 and the receiving circuits 61, 64 are implemented as tri-state circuits.

In a first operating state, the receiving circuit 61 and the transmitting circuit 63 are switched to high resistance. Consequently, in the first operating state, the first coil 62 is operated as the transmitting coil and the second coil 65 is operated as the receiving coil, wherein the transmitting and receiving coils are coupled via a ring-shaped electrical current 66 in the medium. In the second operating state, in contrast, the transmitting circuit 60 and the receiving circuit 64 are switched to high resistance. Consequently, in the second operating state, the second coil 65 is operated as the transmitting coil, and the first coil 62 is operated as the receiving coil.

Figure 7A:
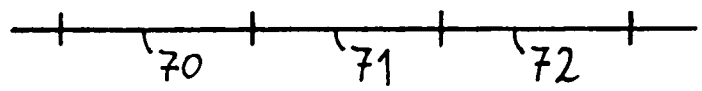
FIG. 7 is a representation of two possible manners of operation of a sensor of the invention.

A conductivity sensor with the switching functionality of the invention can be operated in different operating modes. In the case of a first mode of operation (which is illustrated in FIG. 7A), the two coils each alternately as employed as transmitting coils. During the time interval 70, the first coil is used as the transmitting coil and the second coil as the receiving coil, wherein the coil parameters of the first coil are simultaneously checked. Optionally, the inductance of the first coil can be ascertained by the transmitting circuit. In the following interval 71, the second coil is operated as the transmitting coil, while the first coil serves as the receiving coil. During this time interval 71, the coil parameters of the second coil can be checked. Optionally, the inductance of the second coil can be ascertained by the transmitting circuit. In the following time interval 72, the first coil then again serves as the transmitting coil, and the second coil is operated as the receiving coil.

Figure 7B:
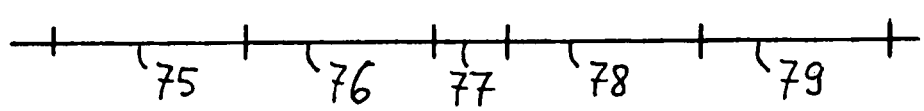

As an alternative to the operational form illustrated in FIG. 7A, in the case of which the roles of the two coils regularly alternate, the first coil can be permanently fixed as the transmitting coil for conductivity measurements. Such a form of embodiment is shown in FIG. 7B. During the time intervals 75 and 76, the first coil is operated as the transmitting coil, and the second coil serves as the receiving coil. During the time intervals 75 and 76, the coil parameters of the first coil can be monitored, and, optionally, the inductance of the first coil can also be ascertained. For reviewing the functionality of the second coil, in the time interval 77, a switching between the transmitting and receiving coils takes place: The first coil becomes the receiving coil, and the second coil becomes the transmitting coil. During the time interval 77, the coil parameters of the second coil can be checked. Then, during the time intervals 78 and 79, the first coil is again operated as the transmitting coil, while the second coil again serves as the receiving coil.

It is possible to specify the time intervals 70 to 79 fixedly. Alternatively, the switching between the intervals—especially the switching between 1) a first interval, in which the first coil is employed as the transmitting coil and the second coil as the receiving coil, wherein the coil parameters of the first coil can simultaneously be checked, and 2) a second interval, in which the second coil is operated as the transmitting coil, while the first coil serves as the receiving coil, and wherein the coil parameters of the second coil can be checked—can be controlled via the signals for determining conductivity and/or the signals for measuring temperature from an additional temperature sensor integrated into the conductivity sensor. The point in time in which the switching occurs can also be controlled via the signals of external measuring and control parameters.

The invention claimed is:

1. An inductively working sensor for determining the conductivity of a liquid medium, comprises:
    at least one transmitting circuit, which is designed to deliver an input signal for a transmitting coil, in order to produce in the transmitting coil an alternating electromagnetic field, which causes a ring-shaped electrical current in the liquid medium;
    at least one receiving circuit, which is designed to evaluate a received signal produced by the ring-shaped electrical current in a receiving coil;
    a first coil; and
    a second coil arranged at a distance from said first coil; and
    switching means for switching between a first switch state and a second switch state, wherein:
    in said first switch state, said first coil, serving as a transmitting coil, is coupled with said at least one transmitting circuit, and said second coil, serving as a receiving coil, is coupled with said at least one receiving circuit; and
    in said second switch state, said second coil, serving as a transmitting coil, is coupled with said at least one transmitting circuit, and said first coil, serving as receiving coil is coupled with said at least one receiving circuit.

2. The inductively working sensor as claimed in claim 1, wherein:
    the ring-shaped electrical current produced in the liquid medium runs through a sensor opening of said sensor;
    said first coil and said second coil are embodied as toroidal coils;
    said first coil and said second coil are as embodied coils in a closed form;
    said first coil and said second coil are arranged coaxially to one another;
    the planes of said first coil and said second coil are arranged parallel to one another;
    said first coil and said second coil are arranged coplanarly, next to one another, and especially axially parallel to one another;
    said first coil and said second coil are arranged inclined toward one another, especially inclined toward one another in such a manner that axes of the coils come together to form an angle of 90°; and
    said first coil and said second coil are arranged coaxially coplanarly.

3. The inductively working sensor as claimed in claims 1, wherein:
    at least one of said transmitting circuits is designed to check a functionality of a coil coupled with said at least one transmitting circuit.

4. The inductively working sensor as claimed in claim 1, wherein:
    at least one of said at least one transmitting circuit is designed to monitor parameters of a coil coupled with said at least one transmitting circuit.

5. The inductively working sensor as claimed in claim 4, wherein:
    at least one of the transmitting circuits is designed to check whether monitored variables lie within predefined range limits.

6. The inductively working sensor as claimed in claim 5, wherein:
    at least one of the transmitting circuits is designed to determine on the basis of electrical current and voltage in the transmitting circuit an inductance of a coil coupled with the transmitting circuit.

7. The inductively working sensor as claimed in claim 1, wherein:
    in the case of a coil coupled with said at least one transmitting circuit, at least one of the transmitting circuits is designed to monitor one or more of the following variables: input signal of the coil; electrical current through the coil; variable signal at the entrance of the coil; inductance of the coil; impedance in said at least one transmitting circuit; reactance in said at least one transmitting circuit; resistance in said at least one transmitting circuit; coil quality of the coil; and variables which can be calculated from the previously set forth variables.

8. The inductively working sensor as claimed in claim 1, wherein:
    in the case of a coil coupled with said at least one transmitting circuit, at least one of the transmitting circuits is designed to detect one or more of the following defects: contact interruption; coil break; winding short or leakage current between neighboring windings; short circuit in supply lines of the coil, in the coil itself or in coil support; damage to a core of the coil; drift or other short- or long-term changes of inductance of the coil; and penetration of the liquid medium into the coil.

9. The inductively working sensor as claimed in claim 1, further comprising:
    an evaluation unit, which, based on the received signal, ascertains conductivity of the liquid medium.

10. The inductively working sensor as claimed in claim 9, wherein:

said evaluation unit is designed to determine conductivity of the liquid medium taking into consideration inductance of said at least one receiving coil and/or inductance of said transmitting coil.

11. The inductively working sensor as claimed in claim 1, wherein:
said switching means is implemented with the assistance of at least one of the following: a mechanical switch or a relay; multiplexer; and a demultiplexer.

12. The inductively working sensor as claimed in claim 1, wherein:
the inductively working sensor includes two transmitting circuits and/or two receiving circuits.

13. The inductively working sensor as claimed in claim 12, wherein:
a transmitting circuit and a receiving circuit are associated with the first coil; and
said switching means is designed to couple said first coil either with the associated transmitting circuit or with the associated receiving circuit.

14. The inductively working sensor as claimed in claim 12, wherein:
a transmitting circuit and a receiving circuit are associated with said second coil; and
said switching means is designed to couple said second coil either with the associated transmitting circuit or with the associated receiving circuit.

15. The inductively working sensor as claimed in claim 12, wherein:
the transmitting circuits and the receiving circuits are embodied according to tri-state technology; and
said switching means is designed to switch at least one of the transmitting circuits and/or at least one of the receiving circuits to a high-resistance state.

16. The inductively working sensor as claimed in claim 1, wherein:
said first coil and said second coil are alternately operated as a transmitting or receiving coil.

17. A method for determining conductivity of a liquid medium by means of an inductively working sensor, wherein the sensor includes: at least one transmitting circuit, which is designed to deliver an input voltage for a transmitting coil; at least one receiving circuit, which is designed to evaluate a received signal produced in a receiving coil; a first coil; and a second coil arranged at a distance from the first coil;
the method comprising the steps of:
connecting the first coil with one of the transmitting circuits for operating the first coil as transmitting coil,
connecting the second coil with one of the receiving circuits for operating the second coil as receiving coil;
producing by the first coil an electromagnetic field, which brings about a ring-shaped electrical current in the liquid medium,
determining conductivity of the liquid medium on the basis of a received signal produced by the ring-shaped electrical current in the second coil; and
connecting the second coil with one of the transmitting circuits for operating the second coil as transmitting coil and connecting the first coil with one of the receiving circuits for operating the first coil as receiving coil.

18. The method as claimed in claim 17, further comprising the step of:
monitoring a functionality of a coil coupled with one of the transmitting circuits.

19. The method as claimed in claim 17, further comprising the step of:
determining inductance of a coil coupled with one of the transmitting circuits.

20. The method as claimed in claim 17, wherein:
a point in time of connecting the second coil with one of the transmitting circuits for operation of the second coil as transmitting coil and of connecting the first coil with one of the receiving circuits for operation of the first coil as receiving coil is controlled via signals received during conductivity measurement and/or via a signal of an additional temperature measurement.

21. The method as claimed in claim 17, wherein:
a point in time of connecting the second coil with one of the transmitting circuits for operation of the second coil as transmitting coil and of connecting the first coil with one of the receiving circuits for operation of the first coil as receiving coil is controlled via signals from external sensors for determining external measuring and control parameters.

* * * * *